United States Patent
Hsu et al.

(10) Patent No.: US 9,746,465 B2
(45) Date of Patent: Aug. 29, 2017

(54) MAGNETIC BEAD-BASED DIGITAL MICROFLUIDIC IMMUNOANALYSIS DEVICE AND METHOD THEREOF

(71) Applicant: National Chiao Tung University, Hsinchu (TW)

(72) Inventors: Wensyang Hsu, Hsinchu (TW); Cheng-Yeh Huang, Hsinchu (TW); Po-Yen Tsai, Hsinchu (TW); Po-Huai Shih, Hsinchu (TW); Shih-Kang Fan, Taipei (TW); Da-Jeng Yao, Hsinchu (TW); Cheng-Hsien Liu, Hsinchu (TW); Hong-Yuan Huang, Taoyuan (TW)

(73) Assignee: National Chiao Tung University, Hsinchu (TW)

( * ) Notice: Subject to any disclaimer, the term of this patent is extended or adjusted under 35 U.S.C. 154(b) by 326 days.

(21) Appl. No.: 14/738,942

(22) Filed: Jun. 15, 2015

(65) Prior Publication Data
US 2016/0274098 A1 Sep. 22, 2016

(30) Foreign Application Priority Data
Mar. 16, 2015 (TW) ............................. 104108305 A

(51) Int. Cl.
*G01N 33/543* (2006.01)
*G01N 27/74* (2006.01)
(Continued)

(52) U.S. Cl.
CPC ..... *G01N 33/54333* (2013.01); *G01N 27/745* (2013.01); *G01N 33/573* (2013.01); *G01N 33/6863* (2013.01)

(58) Field of Classification Search
CPC ......... G01N 33/54333; G01N 33/6863; G01N 33/573; G01N 27/745
See application file for complete search history.

(56) References Cited

U.S. PATENT DOCUMENTS 7,572,355 B1 *  8/2009  Arumugam ......... B01F 13/0077
                                                            204/401
7,816,121 B2   10/2010  Pollack et al.
(Continued)

FOREIGN PATENT DOCUMENTS

CN    101375166    2/2009
CN    102866193    1/2013
(Continued)

OTHER PUBLICATIONS

C.T.Lim, et al., "Bead-based microfluidic immunoassays: The next generation," Biosensors & Bioelectronics (Impact Factor: 6.41), vol. 22, No. 7, Mar. 2007, pp. 1197-1204.
(Continued)

*Primary Examiner* — Arun S Phasge
(74) *Attorney, Agent, or Firm* — Jianq Chyun IP Office

(57) ABSTRACT

A magnetic bead-based digital microfluidic immunoanalysis device and a method thereof are provided, which includes a lower plate, an upper plate disposed above the lower plate, a separating structure therebetween and a magnet disposed on the upper plate or the lower plate. The lower plate includes a first electrode layer including a plurality of channel electrodes with different sizes. A droplet containing few magnetic beads is adapted to be disposed on the lower plate and corresponding to the channel electrodes. The magnet attracts the magnetic beads to approach to the smaller one of the channel electrodes though a magnetic force, and when a voltage is applied to the first electrode layer, the droplet is divided to a detection portion with the magnetic beads and a waste-liquid portion without the magnetic beads respectively corresponding to the smaller one and the larger one of the channel electrodes through a dual-direction electrowetting-on-dielectric force.

19 Claims, 9 Drawing Sheets

(51) Int. Cl.
    *G01N 33/573*    (2006.01)
    *G01N 33/68*    (2006.01)

(56) References Cited

U.S. PATENT DOCUMENTS

| | | |
|---|---|---|
| 8,313,895 B2 | 11/2012 | Pollack et al. |
| 8,389,297 B2 | 3/2013 | Pamula et al. |
| 8,492,168 B2 | 7/2013 | Srinivasan et al. |
| 8,637,317 B2 | 1/2014 | Pamula et al. |
| 8,685,754 B2 | 4/2014 | Pollack et al. |

FOREIGN PATENT DOCUMENTS

| | | |
|---|---|---|
| CN | 103348245 | 10/2013 |
| TW | 182031 | 4/1992 |
| TW | 594007 | 6/2004 |
| TW | I296713 | 5/2008 |

OTHER PUBLICATIONS

Helene Andersson, et al., "Micromachined flow-through filter-chamber for chemical reactions on beads," Sensors and Actuators B, vol. 67, Issues 1-2, Aug. 10, 2000, pp. 203-208.

"Office Action of Taiwan Counterpart Application," dated Feb. 15, 2016, p. 1-p. 3.

Ramakrishna S. Sista, et al., "Heterogeneous immunoassays using magnetic beads on a digital microfluidic platform," Lab Chip, Dec. 2008, pp. 2188-pp. 2196.

Ramakrishna S. Sista, et al., "Development of a digital microfluidic platform for point of care testing," Lab Chip, Dec. 2008, pp. 2091-pp. 2104.

Alphonsus H. C. Ng, et al., "Digital Microfluidic Magnetic Separation for Particle-Based Immunoassays," Anal. Chem., vol. 84, Oct. 2012, pp. 8805-pp. 8812.

Kihwan Choi, et al., "Automated Digital Microfluidic Platform for Magnetic-Particle-Based Immunoassays with Optimization by Design of Experiments," Anal. Chem. vol. 85, Aug. 2013, pp. 9638-pp. 9646.

Nicolas Vergauwe, et al., "A highly efficient extraction protocol for magnetic particles on a digital microfluidic chip," Sens. Actuator B-Chem., vol. 196, Jun. 2014, pp. 282-pp. 291.

Po-Yen Tsai, "Digital micro-fluidic chip for bead-based immunoassay with low bead number," a Thesis Submitted to Department of Mechanical Engineering, College of Engineering, National Chiao Tung University, Sep. 2014.

\* cited by examiner

MAGNETIC BEAD-BASED DIGITAL MICROFLUIDIC IMMUNOANALYSIS DEVICE AND METHOD THEREOF

CROSS-REFERENCE TO RELATED APPLICATION

This application claims the priority benefit of Taiwan application serial no. 104108305, filed on Mar. 16, 2015. The entirety of the above-mentioned patent application is hereby incorporated by reference herein and made a part of this specification.

BACKGROUND OF THE INVENTION

Field of the Invention

The present invention relates to a microfluidic immunoanalysis device and method thereof, and relates particularly to a magnetic bead-based digital microfluidic immunoanalysis device and method thereof.

Description of Related Art

In recent years, immunoassay has become one of the most commonly used detection methods in laboratories, and may be used for detecting the concentration of target objects in biological fluids. The principle of immunoassay is in fixing a capture antibody on a solid phase carrier and adding a target antigen as a target. At this time, the capture antibody on the solid phase carrier and the target antigen acting as the target make a specific bonding, and then the excess substance not bonded is washed and removed. Next, a detection antibody having labels is added to make a specific bonding with the target antigen acting as the target, and then the excess substance not bonded is washed and removed, and whether the target remains is observed and quantified.

A magnetic bead-based digital microfluidic immunoanalysis chip uses magnetic beads as the aforementioned solid phase carrier, and is operated by arranging with a microfluidic system. The main advantages being the amount of sample liquid and detection time required may be significantly reduced. However, before performing the aforementioned washing process, current magnetic bead-based digital microfluidic immunoanalysis chips typically use a single-direction electrowetting-on-dielectric technique or a dual-direction electrowetting-on-dielectric technique to separate the excess waste-liquid. The single-direction electrowetting-on-dielectric technique refers to applying a voltage at one side of a droplet and using a magnetic force to fix the magnetic beads in the droplet, and then removing the excess waste-liquid from the droplet. However, this technique is unable to fix the magnetic beads to persist in the droplet through a magnetic force, so that parts of the magnetic beads are removed along with the excess waste-liquid. Similarly, the dual-direction electrowetting-on-dielectric technique refers to applying a voltage at two respective sides of a droplet to divide the droplet to two portions, and using a magnetic force to fix the magnetic beads in one of the portions and removing the other portion from the droplet as waste-liquid. However, in this technique, the electrodes used for applying a voltage typically are the same size; therefore the two portions divided from the droplet are similar in size, such that part of the magnetic beads still may be removed along with the excess waste-liquid. In this way, current magnetic bead-based digital microfluidic immunoanalysis chips use large amounts of magnetic beads in order to lower the percentage of leaked magnetic beads to lower the effect that leaked magnetic beads has, however the situation of leaked magnetic beads is still unable to be prevented.

Furthermore, when current magnetic bead-based digital microfluidic immunoanalysis chips perform detection, the magnetic beads are dispersed to perform detection, and therefore have the below deficiencies: under conditions where the same amount of sample is used, more magnetic beads are used making the sample disperse on each magnetic bead, such that the labels are dispersed on each magnetic bead and lowering the detection signal of each magnetic bead. In addition, under conditions where the same number of magnetic beads is used, the method of dispersing magnetic beads in the droplet for performing detection makes the detection signal more dispersed. In particular, low concentration conditions may cause the detection signal to be lower than the detection limits of the measuring apparatus and the detection signal may be unable to be measured.

SUMMARY OF THE INVENTION

The invention provides a magnetic bead-based digital microfluidic immunoanalysis device and a method of magnetic bead-based digital microfluidic immunoanalysis, adapted for performing digital microfluidic immunoanalysis with a few magnetic beads, and lowering the probability of leakage of magnetic beads.

The invention provides a magnetic bead-based digital microfluidic immunoanalysis device, adapted for performing digital microfluidic immunoanalysis with a few magnetic beads, including a lower plate, an upper plate, a separating structure and a magnet. The lower plate includes a first electrode layer. The first electrode layer includes a plurality of channel electrodes separated from each other and arranged sequentially. The channel electrodes are of different sizes. A droplet containing the magnetic beads is adapted to be disposed on the lower plate and corresponding to the channel electrodes. The upper plate is disposed above the lower plate, and includes a second electrode layer facing the first electrode layer. The separating structure is disposed between the upper plate and the lower plate, to separate the upper plate and the lower plate. The magnet is disposed on the upper plate or the lower plate, and attracting the magnetic beads to approach the smaller one of the channel electrodes through a magnetic force. When a voltage is applied at the first electrode layer, the droplet is divided to a detection portion with the magnetic beads and a waste-liquid portion without the magnetic beads respectively corresponding to the smaller one and the larger one of the channel electrodes through a dual-direction electrowetting-on-dielectric force.

The invention provides a magnetic bead-based digital microfluidic immunoanalysis device, adapted for performing digital microfluidic immunoanalysis with a few magnetic beads, including a lower plate, an upper plate, a separating structure and a magnet. The lower plate includes a first electrode layer. The first electrode layer includes a plurality of channel electrodes separated from each other and arranged sequentially, in which the channel electrodes are of different sizes. A droplet containing the magnetic beads is adapted to be disposed on the lower plate and corresponding to the channel electrodes. The upper plate is disposed above the lower plate, and includes a second electrode layer facing the first electrode layer. The separating structure is disposed between the upper plate and the lower plate, to separate the upper plate and the lower plate. The magnet is disposed on the upper plate or the lower plate, and attracting the magnetic beads to approach the smaller one of the channel electrodes through a magnetic force. When a voltage is applied at the first electrode layer, the droplet is divided to a detection portion with the magnetic beads and a waste-liquid portion without the magnetic beads respectively corresponding to the smaller one and the larger one of the channel electrodes through a dual-direction electrowetting-on-dielectric force, and the magnet attracts and gathers the magnetic beads in the detection portion for detection.

The invention provides a method of magnetic bead-based digital microfluidic immunoanalysis, adapted for performing digital microfluidic immunoanalysis with a few magnetic beads, including the following step: generating a droplet containing the magnetic beads on a lower plate, wherein the lower plate includes a first electrode layer, the first electrode layer includes a plurality of channel electrodes separated from each other and arranged sequentially, in which the channel electrodes are of different sizes, and the droplet is corresponding to the channel electrodes; attracting the magnetic beads to approach the smaller one of the channel electrodes through a magnetic force of a magnet, and applying a voltage at the first electrode layer, such that the droplet is divided to a detection portion with the magnetic beads and a waste-liquid portion without the magnetic beads respectively corresponding to the smaller one and the larger one of the channel electrodes through a dual-direction electrowetting-on-dielectric force.

The invention provides a method of magnetic bead-based digital microfluidic immunoanalysis, adapted for performing digital microfluidic immunoanalysis with a few magnetic beads, including the following steps: generating a droplet containing the magnetic beads on a lower plate, wherein the lower plate includes a first electrode layer, the first electrode layer includes a plurality of channel electrodes separated from each other and arranged sequentially, in which the channel electrodes are of different sizes, and the droplet is corresponding to the channel electrodes; attracting the magnetic beads to approach the smaller one of the channel electrodes through a magnetic force of a magnet, and applying a voltage at the first electrode layer, such that the droplet is divided to a detection portion with the magnetic beads and a waste-liquid portion without the magnetic beads respectively corresponding to the smaller one and the larger one of the channel electrodes through a dual-direction electrowetting-on-dielectric force; attracting and gathering the magnetic beads in the detection portion for detection through the magnet.

Based on the above, in the magnetic bead-based digital microfluidic immunoanalysis device and method thereof of the invention, the first electrode layer uses a plurality of channel electrodes of different sizes, and a droplet containing a few magnetic beads corresponds to the channel electrodes. In this way, the magnet attracts the magnetic beads to correspond to the smaller one of the channel electrodes, and when a voltage is applied to the first electrode layer, the droplet is divided to a detection portion with magnetic beads and a waste-liquid portion without magnetic beads respectively corresponding to the smaller one and the larger one of the channel electrodes through a dual-direction electrowetting-on-dielectric force. Therefore, the magnetic beads persist at the detection portion (corresponding to the smaller one of the channel electrodes) and are not separated from the droplet along with the waste-liquid portion. In this way, the magnetic bead-based digital microfluidic immunoanalysis device and the method thereof are adapted for performing digital microfluidic immunoanalysis with a few magnetic beads, and the probability of leakage of the magnetic beads is lowered.

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1:
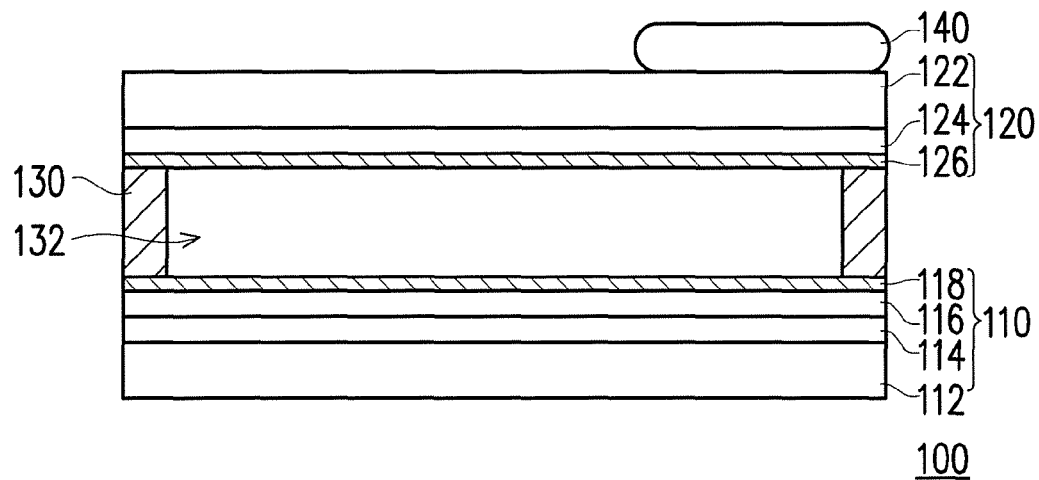
FIG. 1 is a schematic side view of a magnetic bead-based digital microfluidic immunoanalysis device according to an embodiment of the invention.
Figure 2:
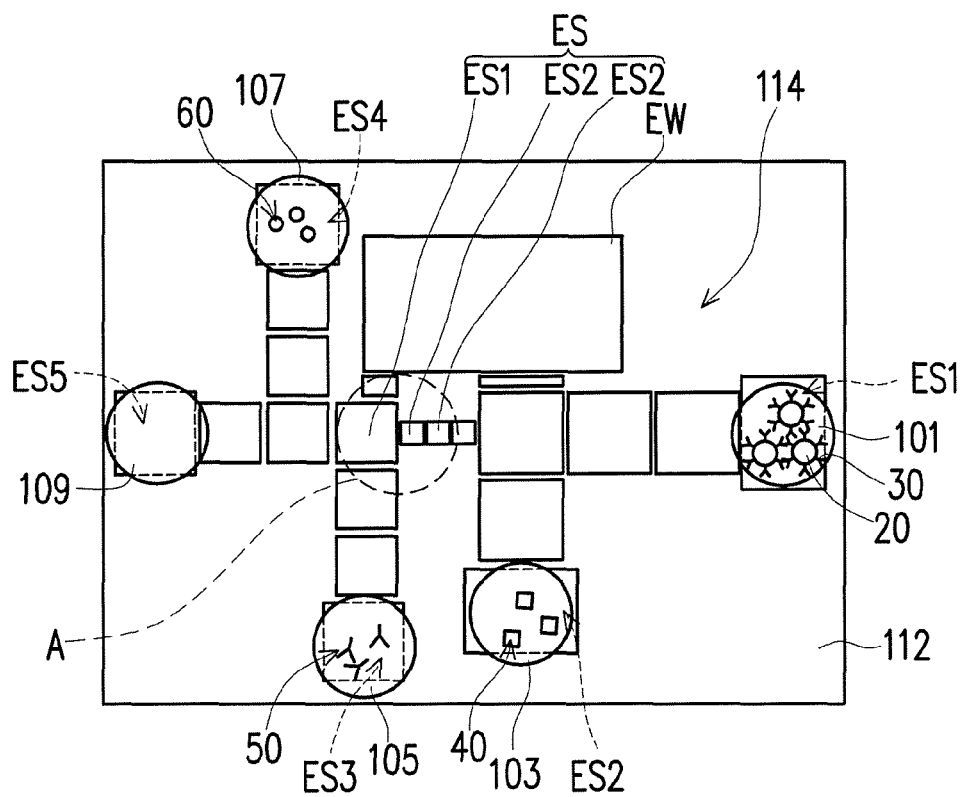
FIG. 2 is a schematic top view of a lower plate of FIG. 1.

FIG. 1 is a schematic side view of a magnetic bead-based digital microfluidic immunoanalysis device according to an embodiment of the invention. Referring to FIG. 1, in the present embodiment, a magnetic bead-based digital microfluidic immunoanalysis device 100 is adapted for performing digital microfluidic immunoanalysis using a few magnetic beads 20 (shown in FIG. 2). Performing digital microfluidic immunoanalysis using a few magnetic beads 20 refers to a number of the magnetic beads 20 used for the present embodiment is fewer than 100, but in actuality the number may be adjusted according to requirements and should not be construed as a limitation to the invention. The magnetic bead-based digital microfluidic immunoanalysis device 100, for example, is a magnetic bead-based digital microfluidic immunoanalysis chip, which includes a lower plate 110, an upper plate 120, a separating structure 130 and a magnet 140. A droplet 101 containing magnetic beads 20 (shown in FIG. 2) is adapted to be disposed on the lower plate 110. The upper plate 120 is disposed above the lower plate 110. The separating structure 130 is disposed between the upper plate 120 and the lower plate 110, to separate the upper plate 120 and the lower plate 110. The magnet 140 may be disposed on the upper plate 120 or the lower plate 110 (FIG. 2 shows the magnet 140 disposed on the upper plate 120 as an example for explanation) for attracting the magnetic beads 20 to fix to a particular position through a magnetic force. In addition, the droplet 101 may be divided to two parts after performing digital microfluidic immunoanalysis, so as to remove an excess waste-liquid portion and retain the detection portion containing the magnetic beads 20 for performing detection (described later in detail).

More specifically, in the present embodiment, the lower plate 110 includes a first substrate 112, a first electrode layer 114, a dielectric layer 116 and a first hydrophobic layer 118. The first substrate 112 may be a rectangular plate. Glass with a lower surface roughness may be adopted as a material of the substrate 112, but a silicon substrate, a poly-dimethylsiloxane (PDMS), polyethylene terephthalate (PET), polyethylene naphthalate (PEN), flexible polymer material or other substrate with good insulation may also be adopted. The first electrode layer 114 is disposed on the first substrate 112 and includes a plurality of electrodes separated from each other (described later in detail). A conductive metal material, for example, copper or chromium, conductive polymer material or conductive oxide material, for example, indium tin oxide (ITO) may be adopted as a material of the first electrode layer 114. The dielectric layer 116 is disposed on the first electrode layer 114 and covers all the electrodes of the first electrode layer 114. Parylene, positive photoresist, negative photoresist, a high dielectric constant material or a low dielectric constant material may be adopted as a material of the dielectric layer 116. Furthermore, the first hydrophobic layer 118 is disposed on the dielectric layer 116 and covers the entire dielectric layer 116. Teflon or other hydrophobic material may be adopted as a material of the first hydrophobic layer 118 to have a lower coefficient of friction for the fluid (for example, the droplet 101), such that the fluid flows thereon. However, the material of the first substrate 112, the first electrode layer 114, the dielectric layer 116 and the first hydrophobic layer 118 should not be construed as a limitation to the invention and may be adjusted according to requirements.

Likewise, in the present embodiment, the upper plate 120 includes a second substrate 122, a second electrode layer 124 and a second hydrophobic layer 126. The second substrate 122 is similar to the first substrate 112, which may be a rectangular plate and adopt a material similar to the first substrate 112 for manufacturing. The second electrode layer 124 is disposed on the second substrate 122 and faces the first electrode layer 114, and covers the entire second substrate 122. In other words, the second electrode layer 124 may adopt a material similar to the first electrode layer 114 for manufacturing, however differs from the first electrode layer 114 which adopts a separated electrodes design in that the second electrode layer 124 is an entire layer electrode and corresponds to all the electrodes of the first electrode layer 114. Furthermore, the second hydrophobic layer 126 is disposed on the second electrode layer 124 and covers the entire second electrode layer 124. The second hydrophobic layer 126 may adopt a material similar to the first hydrophobic layer 118 for manufacturing, such that fluid (for example, the droplet 101) flows thereon. However, the material of the second substrate 122, the second electrode layer 124 and the second hydrophobic layer 126 should not be construed as a limitation to the invention and may be adjusted according to requirements.

Furthermore, in the present embodiment, the upper plate 120 is disposed above the lower plate 110 and is arranged in parallel with the lower plate 110, such that the first hydrophobic layer 118 faces the second hydrophobic layer 126. The separating structure 130 is disposed between the lower plate 110 and the upper plate 120 to separate the upper plate 120 and the lower plate 110 and constitute an accommodating space 132 for placing a fluid (such as the droplet 101) therebetween. The separating structure 130 may be a continuous frame type structure and may also be a plurality of separated columnar structures for providing a support and separation function, the specific structure of the separating structure 130 should not be construed as a limitation to the invention. In addition, in the present embodiment, the magnet 140 is disposed on the upper plate 120 for attracting the magnetic beads 20 (shown in FIG. 2) to fix to a particular position through a magnetic force, however in other embodiments, the magnet 140 may also be disposed on the lower plate 110, and similarly has a function for attracting the magnetic beads 20 to fix to a particular position through a magnetic force. In this way, the location of the magnet 140 on the upper plate 120 or the lower plate 110 may be adjusted for manipulating the magnetic beads 20 to move and gather towards a particular direction or location of the magnet 140.

FIG. 2 is a schematic top view of a lower plate of FIG. 1, wherein the dielectric layer 116 and the first hydrophobic layer 118 shown in FIG. 1 are omitted in the lower plate 110 shown in FIG. 2 to clearly show the design and arranging method of the electrodes of the first electrode layer 114 on the first substrate 112. Referring to FIG. 2, in the present embodiment, the first electrode layer 114 includes a plurality of channel electrodes EC, five storage-liquid electrodes ES1 to ES5 and a waste-liquid electrode EW. The channel electrodes EC, the storage-liquid electrodes ES1 to ES5 and the waste-liquid electrode EW are separated from each other and arranged sequentially in intervals on the first substrate 112. The channel electrodes EC are of different sizes, and the droplet 101 containing the magnetic beads 20 is adapted to be disposed on the lower plate 110 and is adapted to move to be corresponding to the channel electrodes EC. Furthermore, the storage-liquid electrodes ES1 to ES5 are separated from each other and each are connected to the channel electrodes EC. The droplet 101 containing the magnetic beads 20, a sample liquid 103, a reagent liquid 105, a labeling liquid 107 and a washing liquid 109 are correspondingly stored in the storage-liquid electrodes ES1 to ES5, and adapted to be mixed together through the channel electrodes EC. In addition, the storage-liquid electrodes ES1 to ES5 are connected with the waste-liquid electrode EW through the channel electrodes EC. After the droplet 101 is mixed with the sample liquid 103, the reagent liquid 105 or the labeling liquid 107, the droplet 101 after mixing may be divided to a detection portion with the magnetic beads 20 and a waste-liquid portion without the magnetic beads 20, then the waste-liquid portion is separated to the waste-liquid electrode EW (described later in detail), and the washing liquid 109 is mixed to the detecting portion for washing.

More specifically, in the present embodiment, the magnetic beads 20 contain a plurality of capture antibodies 30, the sample liquid 103 contains a plurality of target antigens 40, the reagent liquid 105 contains a plurality of detection antibodies 50, and the labeling liquid 107 contains a plurality of labels 60. The capture antibodies 30, the target antigens 40, the detection antibodies 50 and the labels 60 use the magnetic beads 20 as a solid phase carrier to perform magnetic bead-based digital microfluidic immunoanalysis. FIG. 2 shows a few magnetic beads 20, the capture antibodies 30, the target antigens 40, the detection antibodies 50 and the labels 60 only as a schematic. The actual numbers may be adjusted according to requirements (for example, the number of the magnetic beads 20 used for the present embodiment is fewer than 100), and the invention is not limited thereto. In this way, the droplet 101 stored at the storage-liquid electrode ES1 is mixed with the sample liquid 103, the reagent liquid 105 or the labeling liquid 107 stored at the storage-liquid electrodes ES2 to ES4 through the channel electrodes EC according to requirements. Furthermore, the capture antibodies 30 on the magnetic beads 20 may be bonded with the target antigens 40 in the sample liquid 103, the target antigens 40 may be bonded with the detection antibodies 50 in the reagent liquid 105, the detection antibodies 50 may be bonded with the labels 60 in the labeling liquid 107, and then the digital microfluidic immunoanalysis performed based on the labels 60.

In this way, in the present embodiment, the droplet 101 may be mixed with one of the sample liquid 103, the reagent liquid 105 and the labeling liquid 107 in sequence. The droplet 101 after mixing may be divided to two portions, namely a detection portion and a waste-liquid portion, such that the excess of the capture antibodies 30, the target antigens 40, the detection antibodies 50 and the labels 60 that are not bonded with each other are separated to the waste-liquid electrode EW along with the waste-liquid portion. And then the washing liquid 109 is mixed to the detection portion for washing. In addition, the magnet 140 may be used to gather the magnetic beads 20 to the detection portion, such that the waste-liquid portion does not contain the magnetic beads 20, and in this way the probability of leakage of the magnetic beads 20 during digital microfluidic immunoanalysis is lowered. Moreover, the labels 60 of the present embodiment, for example, are fluorescent bodies; however the invention is not limited thereto. After the mixing steps are all completed and the excess waste-liquid is divided and separated out, the magnet 140 may attract and gather the magnetic beads 20 in the detection portion, to detect the fluorescent amount of the fluorescent bodies on the magnetic beads 20 and perform digital microfluidic immunoanalysis.

As described above, in the present embodiment, the droplet 101 after mixing may be divided to the detection portion with the magnetic beads 20 and the waste-liquid portion without the magnetic beads 20 and separating out the excess waste-liquid portion, and the magnetic beads 20 of the detection portion are attracted and gathered through the magnet 140 for performing digital microfluidic immunoanalysis. In actuality, the method for dividing in the present embodiment adopts a modified dual-direction electrowetting-on-dielectric force to divide the droplet 101. The modified dual-direction electrowetting-on-dielectric force differs from the single-direction electrowetting-on-dielectric technique in the prior art or a typical dual-direction electrowetting-on-dielectric technique, and the actual method of operating thereof is as follows.

Figure 3:
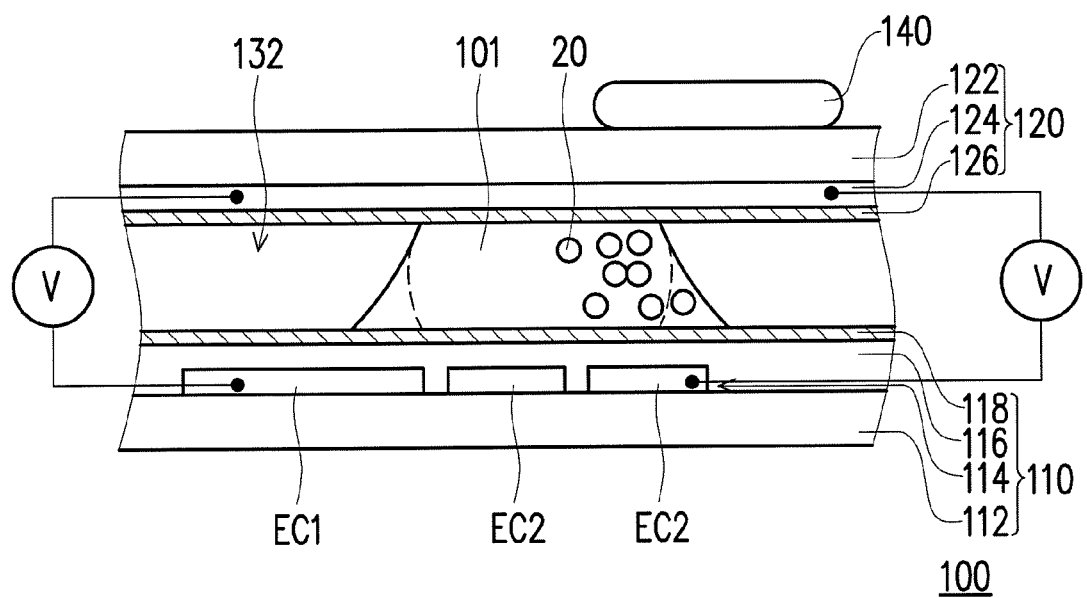
FIG. 3 is a partial schematic side view of the magnetic bead-based digital microfluidic immunoanalysis device of FIG. 1 generating a magnetic force through a magnet and receiving a voltage for generating a dual-direction electrowetting-on-dielectric force.
Figure 4A:
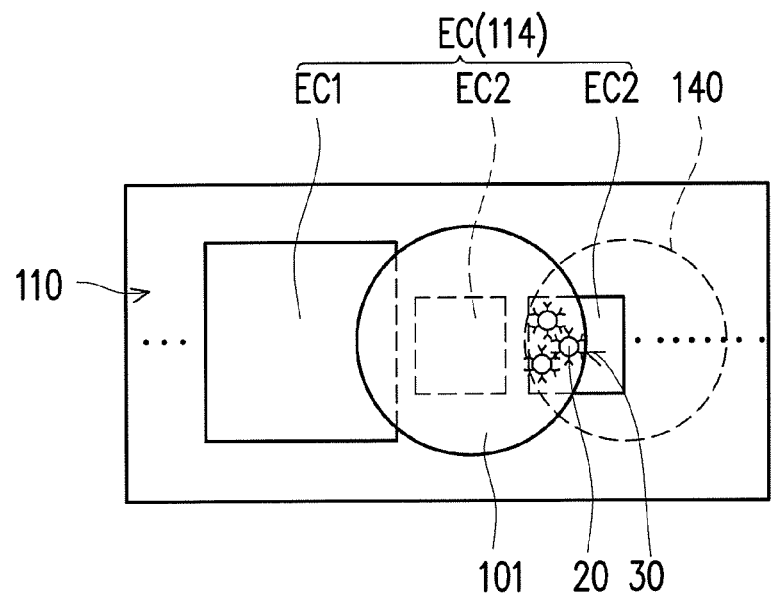
FIG. 4A and FIG. 4B are partial schematic top views of the magnetic bead-based digital microfluidic immunoanalysis device of FIG. 3 gathering magnetic beads through a magnetic force and dividing a droplet through a dual-direction electrowetting-on-dielectric force.
Figure 4B:
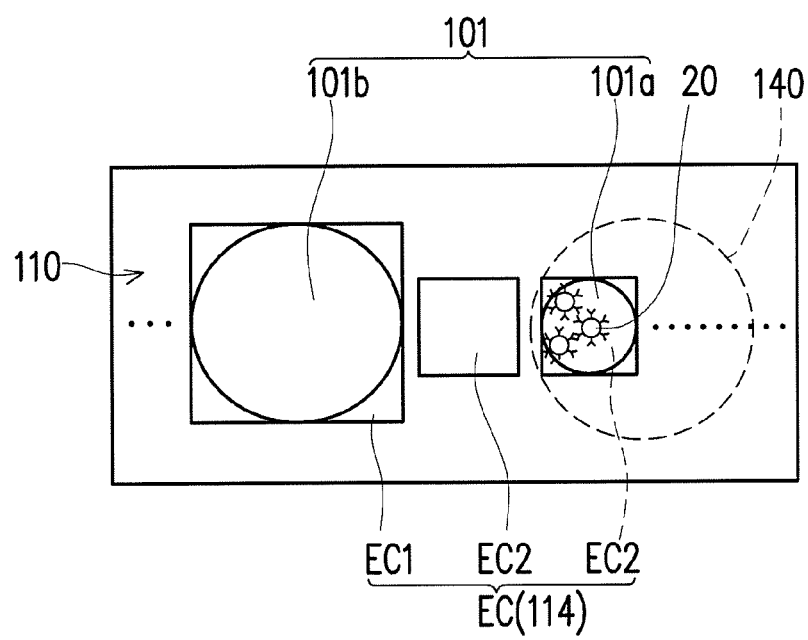

FIG. 3 is a partial schematic side view of the magnetic bead-based digital microfluidic immunoanalysis device of FIG. 1 generating a magnetic force through a magnet and receiving a voltage for generating a dual-direction electrowetting-on-dielectric force. FIG. 4A and FIG. 4B are partial schematic top views of the magnetic bead-based digital microfluidic immunoanalysis device of FIG. 3 gathering magnetic beads through a magnetic force and dividing droplets through a dual-direction electrowetting-on-dielectric force. FIG. 3, FIG. 4A and FIG. 4B show partial schematic diagrams corresponding to a region A of FIG. 2 of the magnetic bead-based digital microfluidic immunoanalysis device 100 of FIG. 1, wherein the other electrodes on the first electrode layer 114 are omitted, for describing the process of generating a magnetic force to attract the magnetic beads 20 through the magnet 140 and generating a dual-direction electrowetting-on-dielectric force to divide the droplet 101 by receiving a voltage.

More specifically, referring to FIG. 2, FIG. 3 and FIG. 4A, in the present embodiment, the channel electrodes EC include at least one first channel electrode EC1 and at least two second channel electrodes EC2, wherein FIG. 2 show a plurality of the first channel electrodes EC1 connected to the storage-liquid electrodes ES1 to ES5 and three of the second channel electrodes EC2 connected with the first channel electrodes EC1 and arranged sequentially, however the invention is not limited thereto. Regarding the channel electrodes EC, the size of the first channel electrodes EC1 are larger than the size of the second channel electrodes EC2. After the droplet 101 is mixed with the sample liquid 103, the reagent liquid 105 and the labeling liquid 107, the droplet 101 after mixing may be moved to be corresponding to the channel electrodes EC. In this way, the droplet 101 after mixing may be corresponding to one of the first channel electrode EC1 and two of the second channel electrodes EC2, for example the region A labeled in FIG. 2. At this time, the magnet 140 is moved to correspond to the smaller channel electrode EC, for example moved to the one of the second channel electrodes EC2 further away from the first channel electrode EC1 (namely the second channel electrode EC2 located on the right side of FIG. 3 and FIG. 4A), to attract the magnetic beads 20 to approach to the smaller one of the channel electrodes EC (namely the one of the second channel electrodes EC2 further away from the first channel electrode EC1/the second channel electrode EC2 located on the right side of FIG. 3 and FIG. 4A). In addition, when a voltage is applied to the first electrode layer 114, the droplet after mixing is divided to a detection portion 101a with magnetic beads 20 and a waste-liquid portion 101b without magnetic beads 20 in the channel electrodes EC through a dual-direction electrowetting-on-dielectric force, and the magnet 140 is corresponding to and attracts the magnetic beads 20 to approach the detection portion.

More specifically, in the present embodiment, the aforementioned applying a voltage to the first electrode layer 114 may refer to applying a voltage between the first electrode layer 114 and the second electrode layer 124 to generate a potential difference, or applying a voltage between different electrodes of the first electrode layer 114, and it should not be construed as a limitation to the invention and may be adjusted according to requirements. When the voltage is applied to the channel electrodes EC of the first electrode layer 114, a portion of the channel electrodes EC generate a dual-direction electrowetting-on-dielectric force, and the droplet 101 after mixing may be divided to a detection portion with the magnetic beads 20 and a waste-liquid portion without the magnetic beads 20. Wherein, due to the different sizes of the channel electrodes EC, therefore the droplet 101 after mixing may be divided to a detection portion with magnetic beads 20 having a smaller volume (corresponding to the smaller one of the channel electrodes EC) and a waste-liquid portion without magnetic beads 20 having a larger volume (corresponding to the larger one of the channel electrodes EC), and then the washing liquid 109 is mixed to the detection portion for washing.

Furthermore, in the present embodiment, the droplet 101 disposed on the lower plate 110 contacts the first hydrophobic layer 118 and the second hydrophobic layer 126. Accordingly, when the first electrode layer 114 has not received a voltage, the droplet 101 (the dotted line shown in FIG. 3) may flow on the first hydrophobic layer 118 and the second hydrophobic layer 126 through the hydrophobic characteristic of the first hydrophobic layer 118 and the second hydrophobic layer 126. When a voltage is applied to the first electrode layer 114, for example, applied between the first electrode layer 114 and the second electrode layer 124 to generate a potential difference between, or applied between different electrodes of the first electrode layer 114, the portion of the first hydrophobic layer 118 corresponding to the spot where the voltage is applied turns hydrophilic, such that the droplet 101 flows towards the portion of the first hydrophobic layer 118 which turned hydrophilic through the electrowetting-on-dielectric force. Wherein, in the present embodiment, the voltage is applied to the first channel electrode EC1 and the one of the second channel electrodes EC2 further away from the first channel electrode EC1 (namely the second channel electrode EC2 located on the right side in FIG. 3 and FIG. 4), such that the portion on the first hydrophobic layer 118 corresponding to the first channel electrode EC1 and the portion corresponding to the one of the second channel electrodes EC2 further away from the first channel electrode EC1 turns hydrophilic, and a dual-direction electrowetting-on-dielectric force is generated. In this way, the droplet 101 moves toward the directions of the first channel electrode EC1 and the one of the second channel electrodes EC2 further away from the first channel electrodes EC1 through the dual-direction electrowetting-on-dielectric force. In other words, two sides of the droplet 101 approaches and moves towards the first channel electrode EC1 and the one of the second channel electrodes EC2 further away from the first channel electrode EC1 respectively, as shown in FIG. 3.

In this way, in the present embodiment, when a voltage is continuously applied to the first electrode layer 114 to increase the dual-direction electrowetting-on-dielectric force, the dual-direction electrowetting-on-dielectric force drives the droplet 101 to move towards the first channel electrode EC1 and the one of the second channel electrodes EC2 further away from the first channel electrode EC1, until the droplet 101 is divided to a detection portion 101a and a waste-liquid portion 101b respectively corresponding to the one of the second channel electrodes EC2 further away from the first channel electrode EC1 and corresponding to the first channel electrode EC1 through the dual-direction electrowetting-on-dielectric force. At this time, because the magnet 140 also attracts the magnetic beads 20 to approach the one of the second channel electrodes EC2 further away from the first channel electrode EC1, therefore the magnetic beads 20 persist in the detection portion 101a, and the waste-liquid portion 101b does not contain magnetic beads 20. Furthermore, the channel electrodes EC of the present embodiment are of different sizes, wherein the size of the first channel electrodes EC1 are larger than the size of the second channel electrodes EC2, and the area ratio of the larger (namely the first channel electrodes EC1) and smaller (namely the second channel electrodes EC2) channel electrodes EC is between 5 to 10 times. In this way, when the droplet 101 is divided to the detection portion 101a corresponding to the one of the second channel electrodes EC2 further away from the first channel electrode EC1 and the waste-liquid portion 101b corresponding to the first channel electrode EC1 through the aforementioned method of generating a dual-direction electrowetting-on-dielectric force, the volume of the detection portion 101a is smaller than the volume of the waste-liquid portion 101b.

Based on the above, in the present embodiment, after the droplet 101 is mixed with the sample liquid 103, the reagent liquid 105 or the labeling liquid 107, arrangement with the first channel electrode EC1 and the second channel electrodes EC2 having designs of different sizes, the droplet 101 after mixing may be divided to the detection portion 101a with magnetic beads 20 having a smaller volume (corresponding to the second channel electrodes EC2 with smaller size) and the waste-liquid portion 101b without magnetic beads 20 having a larger volume (corresponding to the first channel electrode EC1 with larger size) through the dual-direction electrowetting-on-dielectric force, and then the washing liquid 109 is mixed to the detection portion 101a for washing. In this way, the detection portion 101a with magnetic beads 20 having a smaller volume may continue to be used in subsequent mixtures or have analysis and detection performed, and the excess large amount of liquid (without the beads 20) is removed as the waste-liquid portion 101b. After the droplet 101 is mixed with the labeling liquid 107 and divided and separated out the waste-liquid portion 101b, and the washing liquid 109 is mixed to the detection portion 101a for washing, then the magnet 140 may further attract and gather the magnetic beads 20 in the detection portion 101a for detection, for example, detecting the fluorescent amount of the fluorescent bodies on the magnetic beads 20. In this way, the magnetic bead-based digital microfluidic immunoanalysis device 100 of the present invention may lower the probability of leakage of the magnetic beads 20 during digital microfluidic immunoanalysis, and increases the detection accuracy thereof, thereby lowering the detection limitations of the digital microfluidic immunoanalysis.

Figure 5:
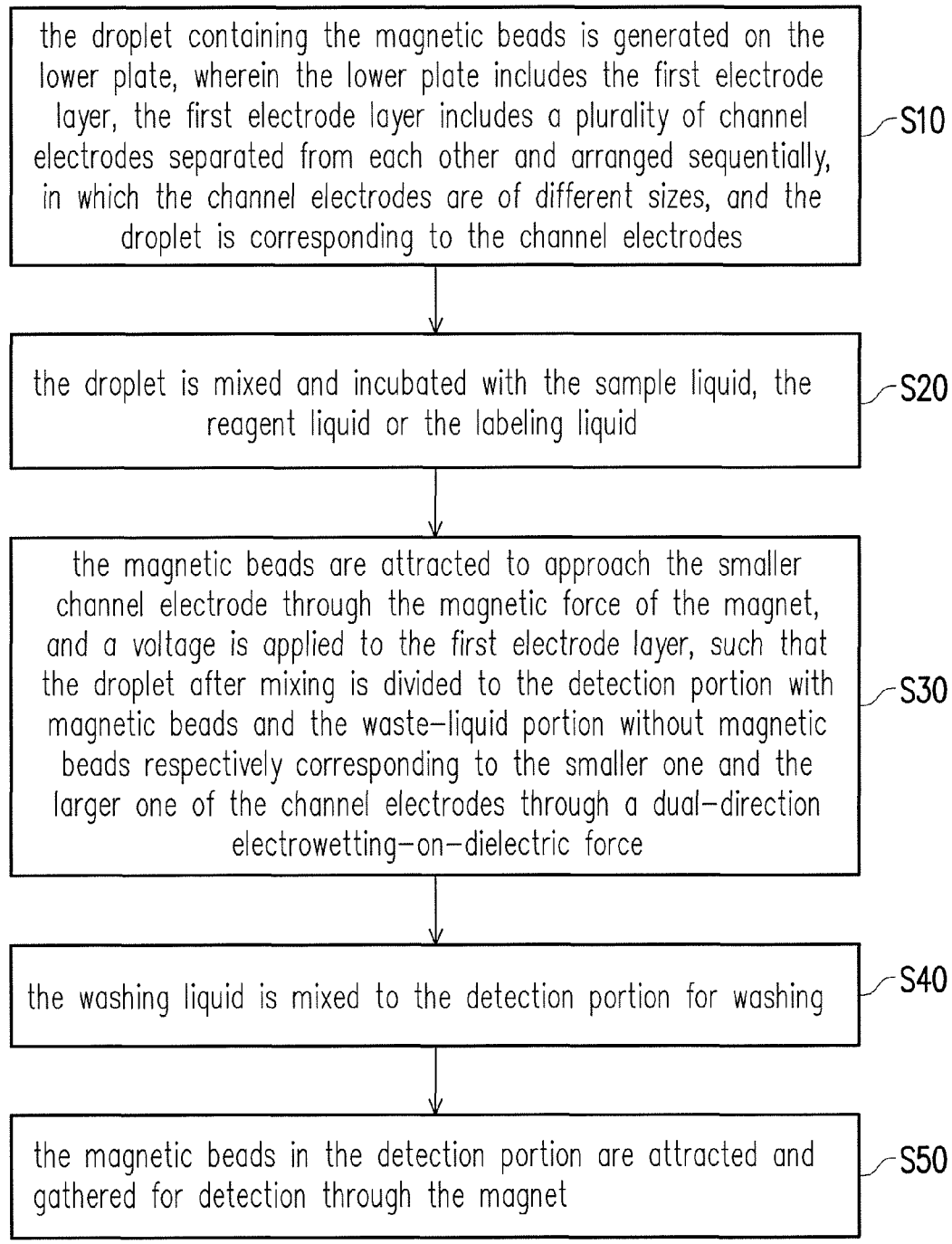
FIG. 5 is a schematic flow diagram of a method of magnetic bead-based digital microfluidic immunoanalysis according to an embodiment of the invention.

FIG. 5 is a schematic flow diagram of a method of magnetic bead-based digital microfluidic immunoanalysis according to an embodiment of the invention. FIG. 6A to FIG. 6J is a schematic flow diagram of the method of magnetic bead-based digital microfluidic immunoanalysis of FIG. 5. Referring to FIG. 5 and FIG. 6A to FIG. 6J, a method of magnetic bead-based digital microfluidic immunoanalysis of the present embodiment is adapted for performing digital microfluidic immunoanalysis with a few magnetic beads 20, and includes the following steps: In a step S10, the droplet 101 containing the magnetic beads 20 is generated on the lower plate 110, wherein the lower plate 110 includes the first electrode layer 114, the first electrode layer 114 includes a plurality of channel electrodes EC separated from each other and arranged sequentially, in which the channel electrodes EC are of different sizes, and the droplet 101 is corresponding to the channel electrodes EC. In a step S20, the droplet 101 is mixed and incubated with the sample liquid 103, the reagent liquid 105 or the labeling liquid 107. In a step S30, the magnetic beads 20 are attracted to approach the smaller channel electrode EC through the magnetic force of the magnet 140, and a voltage is applied to the first electrode layer 114, such that the droplet 101 after mixing is divided to the detection portion 101a with magnetic beads 20 and the waste-liquid portion 101b without magnetic beads 20 respectively corresponding to the smaller one and the larger one of the channel electrodes EC through a dual-direction electrowetting-on-dielectric force. In a step S40, the washing liquid 109 is mixed to the detection portion 101a for washing. In a step S50, the magnetic beads 20 in the detection portion 101a are attracted and gathered for detection through the magnet 140. FIG. 5 and FIG. 6A to FIG. 6J are arranged with FIG. 1 to FIG. 4 to describe the method of magnetic bead-based digital microfluidic immunoanalysis of the present embodiment below.

Figure 6A:
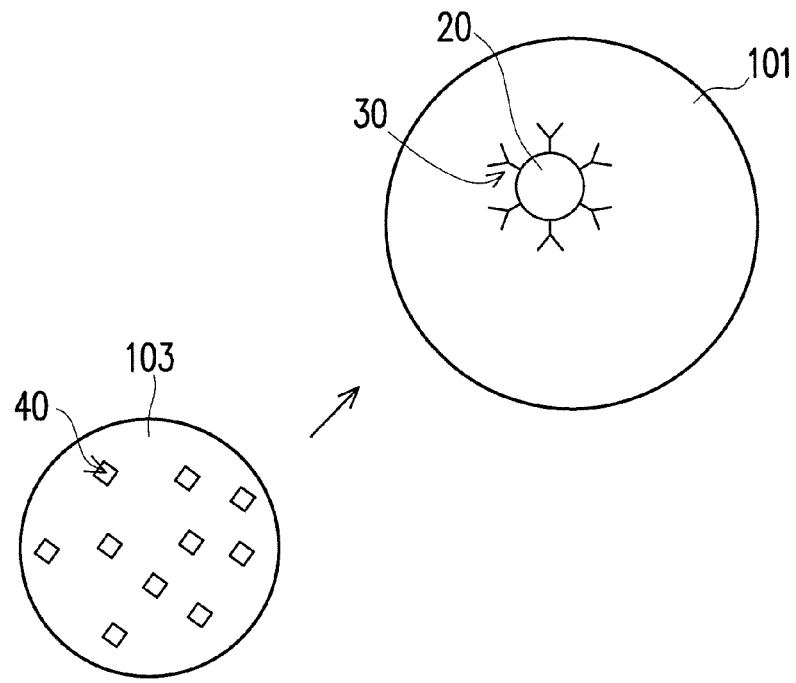
FIG. 6A to FIG. 6J is a schematic flow diagram of the method of magnetic bead-based digital microfluidic immunoanalysis of FIG. 5.
Figure 6B:
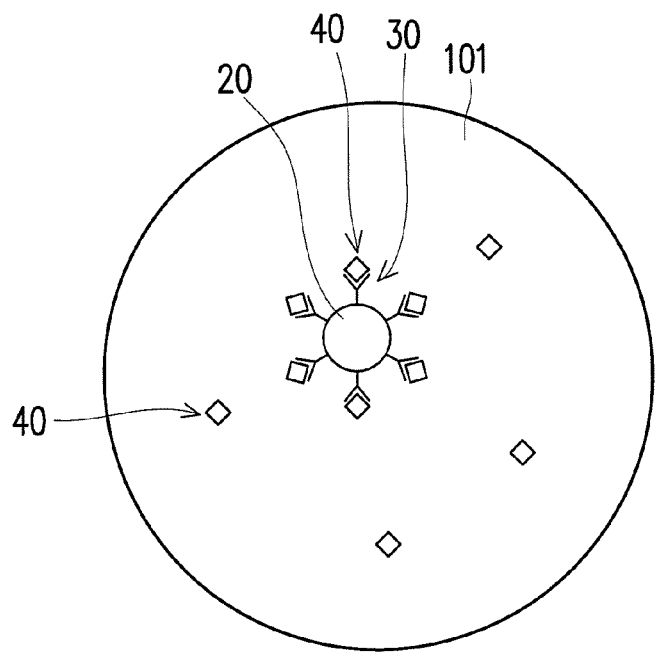
Figure 6C:
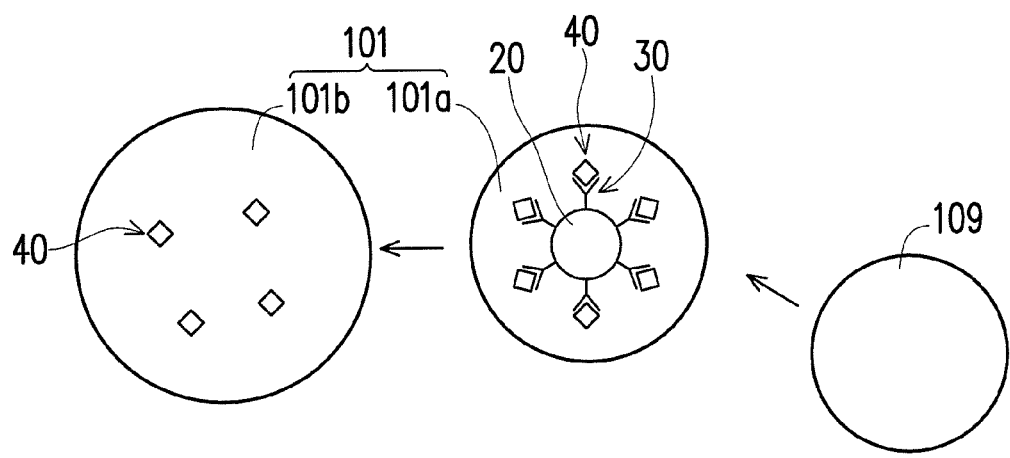
Figure 6D:
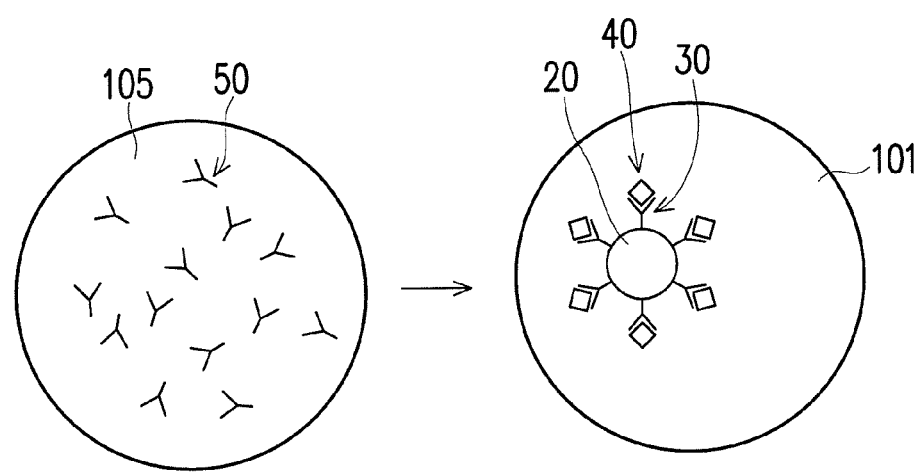
Figure 6E:
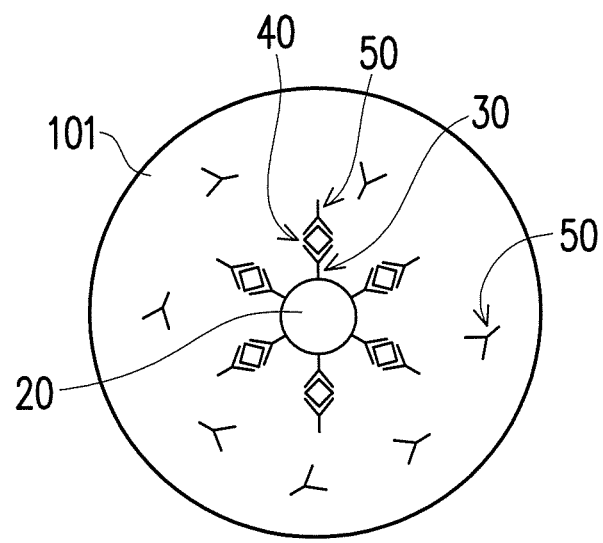
Figure 6F:
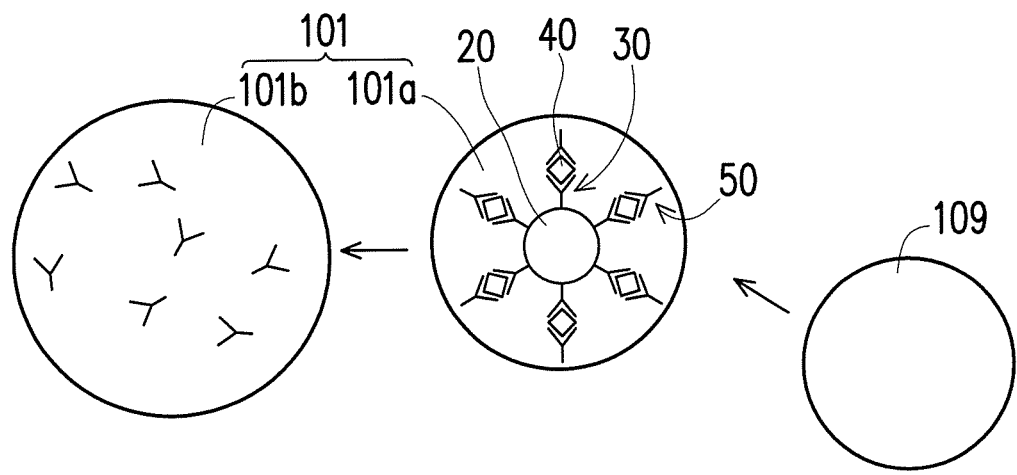
Figure 6G:
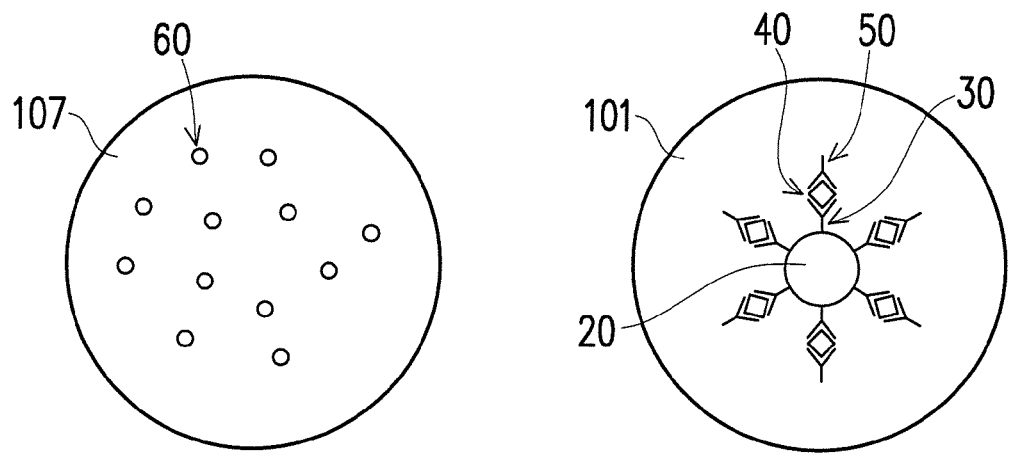
Figure 6H:
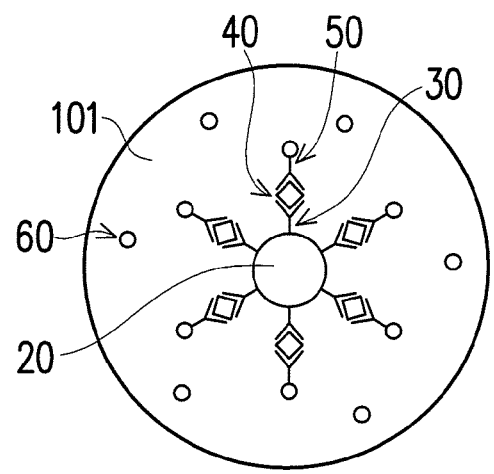
Figure 6I:
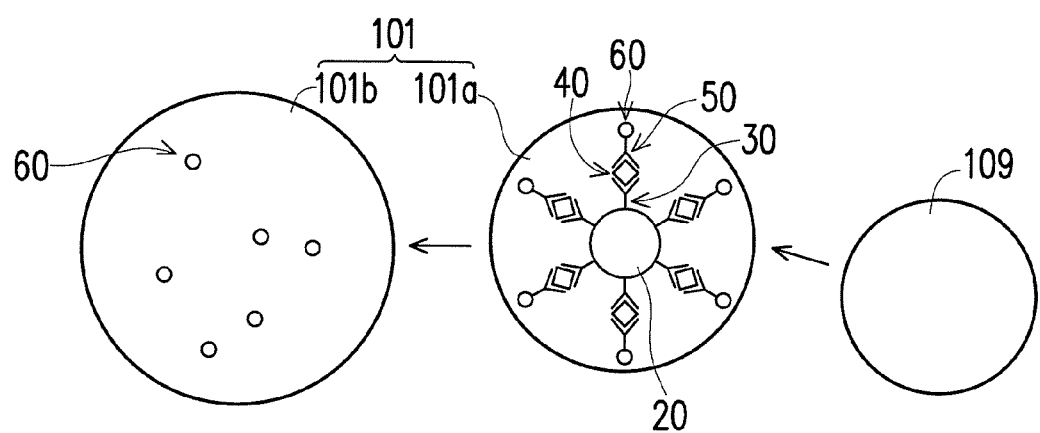

Firstly, referring to FIG. 2, FIG. 5 and FIG. 6A, in the step S10, the droplet 101 containing the magnetic beads 20 is generated on the lower plate 110 (shown in FIG. 2), wherein the lower plate 110 includes the first electrode layer 114, the first electrode layer 114 includes a plurality of channel electrodes EC separated from each other and arranged sequentially, in which the channel electrodes EC are of different sizes, and the droplet 101 is corresponding to the channel electrodes EC. In the present embodiment, although FIG. 6A shows one magnetic bead 20 as a schematic, however in actuality the droplet 101 generated in this step contains a plurality of magnetic beads 20, but the number thereof is fewer than 100. If the droplet 101 generated in this step contains magnetic beads 20 more than 100, then a new droplet 101 is generated again until the magnetic beads 20 contained therein is fewer than 100.

Furthermore, in the present embodiment, the droplet 101 containing the magnetic beads 20 in actuality is generated at the storage-liquid electrode ES1 of the first electrode layer 114, and the magnetic beads 20 contain a plurality of capture antibodies 30 (as shown in FIG. 2). More specifically, the step of generating the droplet 101 containing the magnetic beads 20 (step S10) further includes generating the droplet 101 containing the magnetic beads 20, the sample liquid 103 containing a plurality of the target antigens 40, the reagent liquid 105 containing a plurality of the detection antibodies 50, the labeling liquid 107 containing a plurality of the labels 60 and the washing liquid 109, which storing at the storage-liquid electrodes ES1 to ES5 of the first electrode layer 114. Wherein, the sample liquid 103, the reagent liquid 105, the labeling liquid 107 and the washing liquid 109 may be stored at the storage-liquid electrodes ES2 to ES5 before generating the droplet 101, and also may be generated at the same time with the droplet 101 or generated after the droplet 101 is generated, and the invention is not limited thereto. After the magnetic bead-based digital microfluidic immunoanalysis device 100 (shown in FIG. 2) generates the droplet 101, the sample liquid 103, the reagent liquid 105, the labeling liquid 107 and the washing liquid 109, the subsequent digital microfluidic immunoanalysis may be performed, for example, the mixing together or separating through the channel electrodes EC (as described later).

Next, referring to FIG. 2 and FIG. 5, in the step S20, the droplet 101 is mixed and incubated with the sample liquid 103, the reagent liquid 105 or the labeling liquid 107. More specifically, in the present embodiment, after the step of generating the droplet 101, the sample liquid 103, the reagent liquid 105, the labeling liquid 107 and the washing liquid 109, the capture antibodies 30, the target antigens 40, the detection antibodies 50 and the labels 60 may use the magnetic beads 20 as a solid phase carrier for performing magnetic bead-based digital microfluidic immunoanalysis. Wherein, the droplet 101, the sample liquid 103, the reagent liquid 105, the labeling liquid 107 or the washing liquid 109 are mixed together through the channel electrodes EC, and reference may be made to FIG. 1 to FIG. 2 and the above related content for description.

Next, referring to FIG. 3 to FIG. 5, in the step S30, the magnetic beads 20 are attracted to approach the smaller channel electrode EC through a magnetic force of the magnet 140, and a voltage is applied to the first electrode layer 114, such that the droplet 101 after mixing is divided to the detection portion 101a with magnetic beads 20 and the waste-liquid portion 101b without magnetic beads 20 respectively corresponding to the smaller one and the larger one of the channel electrodes EC through a dual-direction electrowetting-on-dielectric force. Then, in the step S40, the washing liquid 109 is mixed to the detection portion 101a for washing.

More specifically, in the present embodiment, the channel electrodes EC includes at least one first channel electrode EC1 and at least two second channel electrodes EC2, in which the size of the first channel electrode EC1 is greater than the size of the second channel electrodes EC2 (as shown in FIG. 3 to FIG. 5). In this way, in the step of attracting the magnetic beads 20 to approach the smaller one of channel electrodes EC through the magnetic force of the magnet 140 (step S30), the magnetic beads 20 are correspondingly to and attracted to approach the one of the second channel electrodes EC2 further away from the first channel electrodes EC1 (namely the second channel electrode EC2 located on the right side of FIG. 4A and FIG. 4B) through the magnet 140. In addition, in the step of applying a voltage to the first electrode layer 114 (step S40), a voltage is applied at the first channel electrodes EC1 and the one of the second channel electrodes EC2 further away from the first channel electrode EC1, such that a dual-direction electrowetting-on-dielectric force is generated at two respective sides of the droplet 101 (as shown in FIG. 3), such that the droplet 101 is divided to the detection portion 101a and the waste-liquid portion 101b respectively corresponding to the one of the second channel electrodes EC2 further away from the first channel electrodes EC1 and the first channel electrodes EC1 through a dual-direction electrowetting-on-dielectric force. In addition, because the size of the first channel electrode EC1 is larger than the size of the second channel electrodes EC2, therefore in the step of dividing the droplet 101 to the detection portion 101a and the waste-liquid portion 101b (step S20), the volume of the detection portion 101a corresponding to the second channel electrodes EC2 is smaller than the volume of the waste-liquid portion 101b corresponding to the first channel electrodes EC1. Reference may be made to FIG. 3 to FIG. 4B and the aforementioned content for related description and will not be repeated here.

Furthermore, as mentioned above, the droplet 101 of the present embodiment may be mixed and incubated with the sample liquid 103, the reagent liquid 105 or the labeling liquid 107 through the step S20, and the droplet 101 after mixing may be divided to the detection portion 101a and the waste-liquid portion 101b through a dual-direction electrowetting-on-dielectric force in the step S30, such that the waste-liquid portion 101b is separated from the droplet 101, and the detection portion 101a may further be mixed with the washing liquid 109 for washing. However, the process of mixing the droplet 101 with the sample liquid 103, the reagent liquid 105 and the labeling liquid 107 has a particular sequence in the present embodiment, such that the capture antibodies 30, the target antigens 40, the detection antibodies 50 and the labels 60 may react sequentially, and after every reaction, the method of removing the excess waste-liquid portion 101b in FIG. 3 to FIG. 4B may be used, and the washing liquid 109 is mixed to the detection portion 101a for washing. The specific embodiments of steps S20 to S40 are further described below.

Referring to FIG. 2, FIG. 5, FIG. 6A and FIG. 6B, after the step of generating the droplet 101 with the magnetic beads 20 at the lower plate 110, the droplet 101 is mixed and incubated with the sample liquid 103, such that the capture antibodies 30 on the magnetic beads 20 are bonded with the target antigens 40 in the sample liquid 103. More specifically, the droplet 101 and the sample liquid 103 are mixed together through the channel electrodes EC, and then incubated for 10 minutes, for the capture antibodies 30 on the magnetic beads 20 to bond with the target antigens 40 in the sample liquid 103. Wherein, the incubating time above is only one of the embodiments, and may be adjusted according to the types, the number or other requirements of the capture antibodies 30 and the target antigens 40, and should not be construed as a limitation to the invention.

Next, referring to FIG. 3 to FIG. 5 and FIG. 6C, the magnetic beads 20 are attracted to approach the smaller one of the channel electrodes EC through the magnet 140, and a voltage is applied at the first electrode layer 114, such that the droplet 101 after mixing is divided to the detection portion 101a with magnetic beads 20 and the waste-liquid portion 101b without magnetic beads 20 through a dual-direction electrowetting-on-dielectric force, and the waste-liquid portion 101b and the target antigens 40 not bonded with the capture antibodies 30 are separated to the waste-liquid electrode EW of the first electrode layer 114. In other words, the droplet 101 is divided to the detection portion 101a with the magnetic beads 20 and the waste-liquid portion 101b without the magnetic beads 20, wherein the magnetic beads 20 on the detection portion 101a contains the capture antibodies 30 and the target antigens 40 bonded together, and the waste-liquid portion 101b contains the excess of the target antigens 40 not bonded to the capture antibodies 30, and is removed from the droplet 101. Then, the washing liquid 109 is mixed to the detection portion 101a for washing and composing the droplet 101.

Next, referring to FIG. 2, FIG. 5, FIG. 6D and FIG. 6E, the droplet 101 is mixed and incubated with the reagent liquid 105, such that the target antigens 40 on the magnetic beads 20 already bonded with the capture antibodies 30 are bonded with the detection antibodies 50 in the reagent liquid 105. More specifically, the droplet 101 after mixing with the sample liquid 103 and separating out the waste-liquid portion 101b, may further be mixed with the reagent liquid 105 through the channel electrodes EC, and then incubated for 5 minutes, such that the target antigens 40 on the magnetic beads 20 already bonded with the capture antibodies 30 are bonded with the detection antibodies 50 in the reagent liquid 105. Similarly, the above incubating time may be adjusted according to the type, the number or other requirements of the capture antibodies 30, the target antigens 40 and the detection antibodies 50, and should not be construed as a limitation to the invention.

Next, referring to FIG. 3 to FIG. 5 and FIG. 6F, the magnetic beads 20 are attracted to approach the smaller one of the channel electrodes EC through the magnet 140, and a voltage is applied at the first electrode layer 114, such that the droplet 101 after mixing is divided to the detection portion 101a with magnetic beads 20 and the waste-liquid portion 101b without magnetic beads 20 through a dual-direction electrowetting-on-dielectric force. The waste-liquid portion 101b and the detection antibodies 50 not bonded with the target antigens 40 are separated to the waste-liquid electrode EW. In other words, the droplet 101 is divided to the detection portion 101a with magnetic beads 20 and the waste-liquid portion 101b without magnetic beads 20, wherein the magnetic beads 20 on the detection portion 101a contains the capture antibodies 30, the target antigens 40 and the detection antibodies 50 bonded together, and the waste-liquid portion 101b contains the excess of the detection antibodies 50 not bonded to the target antigens 40, and is removed from the droplet 101. Then, the washing liquid 109 is mixed to the detection portion 101a for washing and composing the droplet 101.

Next, referring to FIG. 2, FIG. 5, FIG. 6G and FIG. 6H, the droplet 101 is mixed and incubated with the labeling liquid 107, such that the detection antibodies 50 on the magnetic beads 20 already bonded with the capture antibodies 30 and the target antigens 40 are bonded with the labels 60 in the labeling liquid 107. More specifically, the droplet 101 after mixing with the sample liquid 103 and the reagent liquid 105 sequentially in sequence and separating out the waste-liquid portion 101b, may be further mixed with the labeling liquid 107 through the channel electrodes EC, and then incubated for 3 minutes, such that the detection antibodies 50 on the magnetic beads 20 already bonded with the capture antibodies 30 and the target antigens 40 are bonded with the labels 60 in the labeling liquid 107. Similarly, the above incubating time may be adjusted according to the types, the number or other requirements of the capture antibodies 30, the target antigens 40, the detection antibodies 50 and the labels 60, and should not be construed as a limitation to the invention.

Next referring to FIG. 3 to FIG. 5 and FIG. 6I, the magnetic beads 20 are attracted to approach the smaller one of the channel electrodes EC through the magnet 140, and a voltage is applied at the first electrode layer 114, such that the droplet 101 after mixing is divided to the detection portion 101a with magnetic beads 20 and the waste-liquid portion 101b without magnetic beads 20 through a dual-direction electrowetting-on-dielectric force. The waste-liquid portion 101b and the labels 60 not bonded with the detection antibodies 50 are separated to the waste-liquid electrode EW. In other words, the droplet 101 is divided to the detection portion 101a with magnetic beads 20 and the waste-liquid portion 101b without magnetic beads 20, wherein the magnetic beads 20 on the detection portion 101a contains the capture antibodies 30, the target antigens 40, the detection antibodies 50 and the labels 60 bonded together, and the waste-liquid portion 101b contains the excess of the labels 60 not bonded to the detection antibodies 50, and is removed from the droplet 101. Then, the washing liquid 109 is mixed to the detection portion 101a for washing and composing the droplet 101.

Figure 6J:
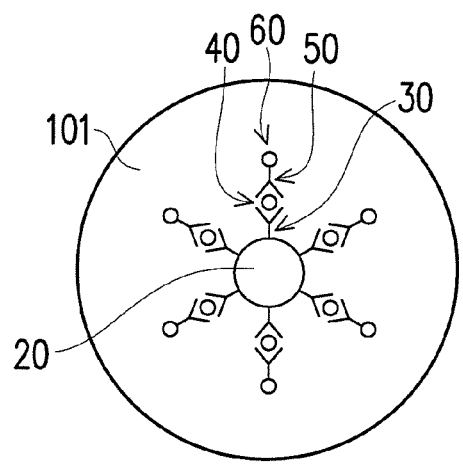

Lastly, in the present embodiment, referring to FIG. 5 and FIG. 6J, in completing the above mixture and incubation, and after dividing and separating out the waste-liquid portion 101b of the droplet 101 through an arrangement of the dual-direction electrowetting-on-dielectric force and magnet force, the magnetic beads 20 in the detection portion 101a may be attracted and gathered for detection through the magnet 140 in step S50. More specifically, in the present embodiment, the labels 60 contained in the labeling liquid 107 may be fluorescent bodies; however the type of labels 60 should not be construed as a limitation to the invention. After the step of mixing the droplet 101 with the labeling liquid 107 and dividing and separating out the waste-liquid portion 101b, and mixing the washing liquid 109 to the detection portion 101a for washing (step S30 and S40), the magnetic beads 20 in the detection portion 101a may be attracted and gathered through the magnet 140 to detect the fluorescent amount of the fluorescent bodies on the magnetic beads 20 in step S50. In this way, the magnetic bead-based digital microfluidic immunoanalysis device 100 of the present embodiment uses a magnetic bead gathering method for performing detection, so as to increase the detection accuracy and lower the detection limitations.

More specifically, in the present embodiment, the aforementioned magnetic bead-based digital microfluidic immunoanalysis device 100 and the method of magnetic bead-based digital microfluidic immunoanalysis may use a few magnetic beads 20 (number fewer than 100) as a solid phase carrier for performing magnetic bead-based digital microfluidic immunoanalysis, wherein a sample liquid required is approximately 200 nL, the detection time required to complete the detection is approximately 1 hour or less, and the detection limit may reach a few pg/mL. When a traditional hole-plate type microfluidic immunoanalysis device analyzes the same sample liquid, a sample liquid of 20 µL to 200 µL is required accommodated by a detection time of 4.5 hours or more. Similarly, when other digital microfluidic immunoanalysis devices analyzes the same sample liquid, a sample liquid of 1.8 µL is required accommodated by a detection time of 65 to 90 minutes or more. It may be seen, the amount of sample liquid required by the magnetic bead-based digital microfluidic immunoanalysis device 100 of the present invention and the method thereof is minimal, and the response thereof is fast and sensitive.

In summary, in the magnetic bead-based digital microfluidic immunoanalysis device and method thereof of the invention, the first electrode layer uses a plurality of channel electrodes of different sizes and a droplet containing a few magnetic beads is corresponding to the channel electrodes. In this way, the magnet attracts the magnetic beads to correspond to the smaller one of the channel electrodes, and when a voltage is applied to the first electrode layer, the droplet is divided to a detection portion with magnetic beads and a waste-liquid portion without magnetic beads respectively corresponding to the smaller one and the larger one of the channel electrodes through a dual-direction electrowetting-on-dielectric force. Therefore, the magnetic beads persist at the detection portion (corresponding to the smaller one of the channel electrodes) and are not separated from the droplet along with the large waste-liquid portion. Furthermore, the invention uses fluorescent bodies as labels, therefore after completing the processes of mixing, incubating, separating the waste-liquid portion and washing by using the magnetic beads as a solid phase carrier, the magnetic beads 20 may be attracted and gathered through the magnet to detect the fluorescent amount of the fluorescent bodies on the magnetic beads, and the detection limitations may be lowered. In this way, the magnetic bead-based digital microfluidic immunoanalysis device is adapted for performing digital microfluidic immunoanalysis with a few magnetic beads, the probability of leakage of the magnetic beads is lowered and the accuracy of the digital microfluidic immunoanalysis is increased.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A magnetic bead-based digital microfluidic immunoanalysis device, adapted for performing digital microfluidic immunoanalysis with a few magnetic beads, comprising:
a lower plate, comprising a first electrode layer, the first electrode layer comprises a plurality of channel electrodes separated from each other and arranged sequentially, in which the channel electrodes are of different sizes, and a droplet containing the magnetic beads is adapted to be disposed on the lower plate and corresponding to the channel electrodes;
an upper plate, disposed above the lower plate, and comprising a second electrode layer facing the first electrode layer;
a separating structure, disposed between the upper plate and the lower plate, to separate the upper plate and the lower plate; and
a magnet, disposed on the upper plate or the lower plate, and attracting the magnetic beads to approach the smaller one of the channel electrodes through a magnetic force, and when a voltage is applied at the first electrode layer, the droplet is divided to a detection portion with the magnetic beads and a waste-liquid portion without the magnetic beads respectively corresponding to the smaller one and the larger one of the channel electrodes through a dual-direction electrowetting-on-dielectric force.

2. The magnetic bead-based digital microfluidic immunoanalysis device as claimed in claim 1, wherein the channel electrodes comprises at least one first channel electrode and at least two second channel electrodes, in which a size of the first channel electrode is larger than a size of the second channel electrodes, and the magnet is corresponding to and attracts the magnetic beads to approach the one of the second channel electrodes further away from the first channel electrode, and the voltage is applied at the first channel electrode and the one of the second channel electrodes further away from the first channel electrode, such that the droplet is divided to the detection portion and the waste-liquid portion respectively corresponding to the one of the second channel electrodes further away from the first channel electrode and the first channel electrode through the dual-direction electrowetting-on-dielectric force.

3. The magnetic bead-based digital microfluidic immunoanalysis device as claimed in claim 1, wherein the first electrode layer comprises a plurality of storage-liquid electrodes, the storage-liquid electrodes are separated from each other, and each are connected to the channel electrodes, and the droplet, a sample liquid, a reagent liquid, a labeling liquid and a washing liquid are correspondingly stored in the storage-liquid electrodes, and adapted to be mixed together through the channel electrodes.

4. The magnetic bead-based digital microfluidic immunoanalysis device as claimed in claim 3, wherein the first electrode layer comprises a waste-liquid electrode, the storage-liquid electrodes are connected with the waste-liquid electrode through the channel electrodes, and after the droplet is mixed with the sample liquid, the reagent liquid or the labeling liquid, the droplet after mixing is divided to the detection portion and the waste-liquid portion through the dual-direction electrowetting-on-dielectric force, then the waste-liquid portion is separated to the waste-liquid electrode, and the washing liquid is mixed to the detection portion for washing.

5. The magnetic bead-based digital microfluidic immunoanalysis device as claimed in claim 3, wherein the magnetic beads contain a plurality of capture antibodies, the sample liquid contains a plurality of target antigens, the reagent liquid contains a plurality of detection antibodies, and the labeling liquid contains a plurality of labels, and the capture antibodies, the target antigens, the detection antibodies and the labels use the magnetic beads as a solid phase carrier for performing digital microfluidic immunoanalysis.

6. The magnetic bead-based digital microfluidic immunoanalysis device as claimed in claim 5, wherein the labels comprises a plurality of fluorescent bodies, after the droplet is mixed with the labeling liquid and divided and separated out the waste-liquid portion, and the washing liquid is mixed to the detection portion for washing, then the magnet attracts and gathers the magnetic beads in the detection portion, so as to detect the amount of fluorescence of the fluorescent bodies on the magnetic beads.

7. The magnetic bead-based digital microfluidic immunoanalysis device as claimed in claim 1, wherein an area ratio of the larger and the smaller channel electrodes is between 5 to 10 times, such that a volume of the detection portion is smaller than a volume of the waste-liquid portion.

8. The magnetic bead-based digital microfluidic immunoanalysis device as claimed in claim 1, wherein a number of the magnetic bead is fewer than 100.

9. A magnetic bead-based digital microfluidic immunoanalysis device, adapted for performing digital microfluidic immunoanalysis with a few magnetic beads, comprising:

a lower plate, comprising a first electrode layer, the first electrode layer comprises a plurality of channel electrodes separated from each other and arranged sequentially, wherein the channel electrodes are of different sizes and a droplet containing the magnetic beads is adapted to be disposed on the lower plate and corresponding to the channel electrodes;

an upper plate, disposed above the lower plate, and comprising a second electrode layer facing the first electrode layer;

a separating structure, disposed between the upper plate and the lower plate, to separate the upper plate and the lower plate; and a magnet, disposed on the upper plate or the lower plate, and attracting the magnetic beads to approach the smaller one of the channel electrodes through a magnetic force, and when a voltage is applied at the first electrode layer, the droplet is divided to a detection portion with the magnetic beads and a waste-liquid portion without the magnetic beads respectively corresponding to the smaller one and the larger one of the channel electrodes through a dual-direction electrowetting-on-dielectric force, and the magnet attracts and gathers the magnetic beads in the detection portion for detection.

10. A method of magnetic bead-based digital microfluidic immunoanalysis, adapted for performing digital microfluidic immunoanalysis with a few magnetic beads, comprising:

generating a droplet containing the magnetic beads on a lower plate, wherein the lower plate comprises a first electrode layer, the first electrode layer comprises a plurality of channel electrodes separated from each other and arranged sequentially, in which the channel electrodes are of different sizes, and the droplet is corresponding to the channel electrodes; and attracting the magnetic beads to approach the smaller one of the channel electrodes through a magnetic force of a magnet, and applying a voltage at the first electrode layer, such that the droplet is divided to a detection portion with the magnetic beads and a waste-liquid portion without the magnetic beads respectively corresponding to the smaller one and the larger one of the channel electrodes through a dual-direction electrowetting-on-dielectric force.

11. The method of magnetic bead-based digital microfluidic immunoanalysis as claimed in claim 10, wherein the channel electrodes comprises at least one first channel electrode and at least two second channel electrodes, in which a size of the first channel electrode is larger than a size of the second channel electrodes, and in the step of attracting the magnetic beads to approach the smaller one of the channel electrodes through the magnet, the magnetic beads are corresponding to and attracted to approach the one of the second channel electrodes further away from the first channel electrode through the magnet, and in the step of applying the voltage at the first electrode layer, the voltage is applied at the first channel electrode and the one of the second channel electrodes further away from the first channel electrode, such that the droplet is divided to the detection portion and the waste-liquid portion respectively corresponding to the one of the second channel electrodes further away from the first channel electrode and the first channel electrode through the dual-direction electrowetting-on-dielectric force.

12. The method of magnetic bead-based digital microfluidic immunoanalysis as claimed in claim 10, further comprising:

generating the droplet containing the magnetic beads, a sample liquid containing a plurality of target antigens, a reagent liquid containing a plurality of detection antibodies, a labeling liquid containing a plurality of labels and a washing liquid storing at a plurality of storage-liquid electrodes of the first electrode layer, and mixing together through the channel electrodes.

13. The method of magnetic bead-based digital microfluidic immunoanalysis as claimed in claim 12, wherein the magnetic beads contain a plurality of capture antibodies, and after the step of generating the droplet, the sample liquid, the reagent liquid, the labeling liquid and the washing liquid, the capture antibodies, the target antigens, the detection antibodies and the labels use the magnetic beads as a solid phase carrier for performing digital microfluidic immunoanalysis.

14. The method of magnetic bead-based digital microfluidic immunoanalysis as claimed in claim 13, further comprising:

mixing and incubating the droplet with the sample liquid, such that the capture antibodies on the magnetic beads are bonded with the target antigens in the sample liquid;

attracting the magnetic beads to approach the smaller one of the channel electrodes through the magnet, and applying a voltage at the first electrode layer, such that the droplet after mixing is divided to the detection portion and the waste-liquid portion through the dual-direction electrowetting-on-dielectric force, and the waste-liquid portion and the target antigens not bonded with the capture antibodies are separated to a waste-liquid electrode of the first electrode layer; and mixing the washing liquid to the detection portion for washing.

15. The method of magnetic bead-based digital microfluidic immunoanalysis as claimed in claim 14, further comprising:

mixing and incubating the droplet with the reagent liquid, such that the target antigens on the magnetic beads already bonded with the capture antibodies are bonded with the detection antibodies in the reagent liquid;

attracting the magnetic beads to approach the smaller one of the channel electrodes through the magnet, and applying a voltage at the first electrode layer, such that the droplet after mixing is divided to the detection portion and the waste-liquid portion through the dual-direction electrowetting-on-dielectric force, and the waste-liquid portion and the detection antibodies not bonded with the target antigens are separated to the waste-liquid electrode; and mixing the washing liquid to the detection portion for washing.

16. The method of magnetic bead-based digital microfluidic immunoanalysis as claimed in claim 15, further comprising:

mixing and incubating the droplet with the labeling liquid, such that the detection antibodies on the magnetic beads already bonded with the capture antibodies and the target antigens are bonded with the labels in the labeling liquid;

attracting the magnetic beads to approach the smaller one of the channel electrodes through the magnet, and applying a voltage at the first electrode layer, such that the droplet after mixing is divided to the detection portion and the waste-liquid portion through the dual-direction electrowetting-on-dielectric force, and the waste-liquid portion and the labels not bonded with the detection antibodies are separated to the waste-liquid electrode; and mixing the washing liquid to the detection portion for washing.

17. The method of magnetic bead-based digital microfluidic immunoanalysis as claimed in claim 16, wherein the labels comprise a plurality of fluorescent bodies, and after the step of mixing the droplet with the labeling liquid, dividing and separating out the waste-liquid portion, and mixing the washing liquid to the detection portion for washing, the magnetic beads in the detection portion are attracted and gathered through the magnet, so as to detect a fluorescent amount of the fluorescent bodies on the magnetic beads.

18. The method of magnetic bead-based digital microfluidic immunoanalysis as claimed in claim 10, wherein in the step of dividing the droplet to the detection portion and the waste-liquid portion, a volume of the detection portion is smaller than a volume of the waste-liquid portion.

19. A method of magnetic bead-based digital microfluidic immunoanalysis, adapted for performing digital microfluidic immunoanalysis with a few magnetic beads, comprising:

generating a droplet containing the magnetic beads on a lower plate, wherein the lower plate comprises a first electrode layer, the first electrode layer comprises a plurality of channel electrodes separated from each other and arranged sequentially, in which the channel electrodes are of different sizes, and the droplet is corresponding to the channel electrodes;

attracting the magnetic beads to approach the smaller one of the channel electrodes through a magnetic force of a magnet, and applying a voltage at the first electrode layer, such that the droplet is divided to a detection portion with the magnetic beads and a waste-liquid portion without the magnetic beads respectively corresponding to the smaller one and the larger one of the channel electrodes through a dual-direction electrowetting-on-dielectric force; and attracting and gathering the magnetic beads in the detection portion for detection through the magnet.

* * * * *